United States Patent
Rosa et al.

(10) Patent No.: US 11,857,326 B2
(45) Date of Patent: Jan. 2, 2024

(54) AGENT-DELIVERING NEURAL PROBE DEVICES AND RELATED SYSTEMS AND METHODS

(71) Applicant: NeuroOne Medical Technologies Corporation, Eden Prairie, MN (US)

(72) Inventors: Dave Rosa, Eden Prairie, MN (US); Thomas Bachinski, Lakeville, MN (US)

(73) Assignee: NeuroOne Medical Technologies Corporation, Eden Prairie, MN (US)

( * ) Notice: Subject to any disclaimer, the term of this patent is extended or adjusted under 35 U.S.C. 154(b) by 535 days.

(21) Appl. No.: 16/812,702

(22) Filed: Mar. 9, 2020

(65) Prior Publication Data

US 2020/0281489 A1  Sep. 10, 2020

Related U.S. Application Data

(60) Provisional application No. 62/815,530, filed on Mar. 8, 2019.

(51) Int. Cl.
*A61B 5/24* (2021.01)
*A61N 1/05* (2006.01)
*A61B 5/00* (2006.01)

(52) U.S. Cl.
CPC .............. *A61B 5/24* (2021.01); *A61N 1/0529* (2013.01); *A61B 5/6868* (2013.01); *A61B 2562/0209* (2013.01)

(58) Field of Classification Search
CPC . A61B 5/24; A61B 5/6868; A61B 2562/0209; A61N 1/0529
See application file for complete search history.

(56) References Cited

U.S. PATENT DOCUMENTS

| | | | | |
|---|---|---|---|---|
| 10,245,178 B1* | 4/2019 | Heitzmann | ......... | A61M 31/002 |
| 2003/0190608 A1* | 10/2003 | Blackburn | .......... | B01L 3/50273 435/7.1 |
| 2004/0043479 A1* | 3/2004 | Briscoe | .............. | G01N 30/6095 435/288.5 |
| 2007/0073357 A1* | 3/2007 | Rooney | .............. | A61N 1/36071 607/46 |
| 2007/0287991 A1* | 12/2007 | McKay | ............ | G01N 33/54366 604/892.1 |
| 2010/0114348 A1* | 5/2010 | Boyden | ................. | G16H 50/50 700/109 |
| 2010/0152880 A1* | 6/2010 | Boyden | .............. | A61K 51/1244 700/283 |
| 2011/0130708 A1* | 6/2011 | Perry | ................. | A61B 18/1492 604/21 |
| 2013/0011332 A1* | 1/2013 | Boyden | ..................... | B26F 1/24 424/9.1 |

(Continued)

*Primary Examiner* — Christopher A Flory
(74) *Attorney, Agent, or Firm* — Fredrikson & Byron, P.A.

(57) ABSTRACT

Provided herein are a variety of neural probe devices that include an agent delivery feature via an agent coating or an agent delivery mechanism of some kind. The probe devices can include depth or cortical probes or electrodes. The agent delivery mechanisms can include, for example, a dissolvable agent delivery structure, an agent delivery lumen, a magnetically deployable cover, an iontophoretic delivery mechanism, an agent delivery cavity defined in the neural probe, or an agent reservoir with an actuable gate.

18 Claims, 8 Drawing Sheets

(56) References Cited

U.S. PATENT DOCUMENTS

| | | | | |
|---|---|---|---|---|
| 2013/0035574 A1* | 2/2013 | Anand | ............... | A61M 5/16804 604/35 |
| 2013/0035660 A1* | 2/2013 | Anand | ............... | A61M 25/0023 604/173 |
| 2013/0310823 A1* | 11/2013 | Gelfand | ............ | A61M 25/0082 606/41 |
| 2014/0200511 A1* | 7/2014 | Boyden | ................. | A61M 37/00 606/213 |
| 2016/0000499 A1* | 1/2016 | Lennox | ................. | A61N 7/022 606/41 |
| 2016/0038940 A1* | 2/2016 | Babcock | ........... | B01L 3/502707 422/68.1 |
| 2016/0144189 A1* | 5/2016 | Bakker | ................ | A61B 5/6868 607/45 |
| 2017/0173262 A1* | 6/2017 | Veltz | ....................... | G16H 20/17 |
| 2017/0245772 A1* | 8/2017 | Bierbrauer | ................ | A61B 5/24 |
| 2017/0246450 A1* | 8/2017 | Liu | ........................ | B05D 1/005 |
| 2020/0008299 A1* | 1/2020 | Tran | ..................... | H05K 1/0386 |

\* cited by examiner

AGENT-DELIVERING NEURAL PROBE DEVICES AND RELATED SYSTEMS AND METHODS

CROSS-REFERENCE TO RELATED APPLICATION

This application claims the benefit under 35 U.S.C. § 119(e) to U.S. Provisional Application 62/815,530, filed Mar. 8, 2019 and entitled "Agent-Delivering Neural Probe Devices and Related Systems and Methods," which is hereby incorporated herein by reference in its entirety.

FIELD

The various embodiments herein relate to neural probes, including agent-delivering neural probes and other neurological treatment devices, including, for example, agent-eluting devices, and related systems and methods for detection and/or stimulation.

BACKGROUND

Known neural probes and devices have relatively thick profiles that can result in damage to the patient's brain tissue during use. Further, any procedure that accesses the human brain triggers a defensive response known as the foreign body response or reaction ("FBR"). This reaction mechanism is a complex signaling system that tells the body to encapsulate the foreign entity and triggers an edema response. The encapsulation isolates the foreign body element from the rest of the surrounding tissue.

There is a need in the art for improved neural probes and related devices and technologies that incorporate agent delivery, including, for example, agent elution.

BRIEF SUMMARY

Discussed herein are various neural probe devices with agent delivery components, including, for example, agent coatings, agent delivery lumens, agent delivery structures disposed over the devices, and other such delivery components, along with related methods of delivering various agents to a patient via such a probe device.

In Example 1, a neural electrode comprises an electrode body, at least one electrode array associated with the electrode body, and a dissolvable agent delivery structure disposed over at least a portion of the electrode body. Example 2 relates to the neural electrode according to Example 1, wherein the dissolvable agent delivery structure is removably disposed over the at least a portion of the electrode body such that the dissolvable agent delivery structure is separable from the electrode body.

Example 3 relates to the neural electrode according to Example 1, wherein the dissolvable agent delivery structure comprises a dissolvable scaffold comprising at least one treatment agent.

Example 4 relates to the neural electrode according to Example 3, wherein the at least one treatment agent is releasable over time as the dissolvable scaffold dissolves.

Example 5 relates to the neural electrode according to Example 3, wherein the at least one treatment agent comprises a cannabinoid.

Example 6 relates to the neural electrode according to Example 1, wherein the electrode body comprises an elongate, unitary tubular body, wherein the at least one electrode array is disposed on an outer surface of the tubular body, and wherein the neural electrode is a depth electrode.

Example 7 relates to the neural electrode according to Example 1, further comprising an elongate structure coupled to the electrode body, wherein the electrode body comprises a thin film pad, wherein the at least one electrode array is disposed in the thin film pad, and wherein the neural electrode is a cortical electrode.

In Example 8, a neural electrode comprises an electrode body, at least one electrode array associated with the electrode body, and a drug delivery component comprising an agent elution coating disposed on the electrode body or a drug delivery lumen defined through a portion of the electrode body.

Example 9 relates to the neural electrode according to Example 8, wherein the electrode body comprises an elongate, unitary tubular body, wherein the at least one electrode array is disposed on an outer surface of the tubular body, and wherein the neural electrode is a depth electrode.

Example 10 relates to the neural electrode according to Example 9, wherein the drug delivery component is the drug delivery lumen, wherein the drug delivery lumen is defined within the elongate tubular body such that the lumen is coaxial with a longitudinal axis of the elongate tubular body, Example 11 relates to the neural electrode according to Example 10, further comprising a drug delivery opening defined at a distal end of the tubular body, wherein the drug delivery opening is in fluidic communication with the drug delivery lumen.

Example 12 relates to the neural electrode according to Example 10, further comprising a plurality of openings defined in the outer surface of the tubular body, wherein the plurality of openings are in fluidic communication with the drug delivery lumen.

Example 13 relates to the neural electrode according to Example 9, wherein the drug delivery component is the agent elution coating, wherein the agent elution coating is disposed on the tubular body.

Example 14 relates to the neural electrode according to Example 13, wherein the agent elution coating comprises at least one treatment agent, wherein the at least one treatment agent is releasable over time.

Example 15 relates to the neural electrode according to Example 8, further comprising an elongate structure coupled to the electrode body, wherein the electrode body comprises a thin film pad, wherein the at least one electrode array is disposed in the thin film pad, and wherein the neural electrode is a cortical electrode.

Example 16 relates to the neural electrode according to Example 15, wherein the drug delivery component is the drug delivery lumen, wherein the drug delivery lumen is defined within the thin film pad.

Example 17 relates to the neural electrode according to Example 15, wherein the drug delivery component is the agent elution coating, wherein the agent elution coating is disposed on the thin film pad.

In Example 18, a method of implanting an intracranial electrode device comprises forming at least one hole in a skull of a patient, urging the intracranial electrode device through the at least one hole, positioning the intracranial electrode device at the target intracranial position, actuating the electrode device to stimulate tissue at the target intracranial position, and delivering an agent to the target intracranial position.

Example 19 relates to the method according to Example 18, wherein the delivering the agent comprises delivering the agent via a dissolvable agent delivery structure, an agent elution coating, or a drug delivery lumen.

Example 20 relates to the method according to Example 18, wherein the agent reduces the inflammation of brain tissue or minimizes or eliminates a seizure.

In Example 21, a neural probe and drug delivery system comprises a neural probe comprising a probe body, a cavity defined in the probe body, and a deployable cover disposed adjacent to the cavity, wherein the deployable cover comprises an open position and a closed configuration in which the deployable cover is disposed over the cavity. Further, the system comprises a magnetic actuation member configured to be disposable near the neural probe, wherein the magnetic actuation member can be in magnetic communication with the deployable cover.

Example 22 relates to the system according to Example 21, wherein an agent is disposable within the cavity.

In Example 23, a neural probe comprises a probe body, a cavity defined in the probe body, a contact disposed within the cavity, an electrical lead operably coupled to the contact, wherein the electrical lead is configuration to allow for transmission of an electrical current, and an ionically polarized agent disposable within the cavity, wherein application of the electrical current is configured to iontophoretically urge the ionically polarized agent out of the cavity.

In Example 24, a neural probe comprises a probe body and a cavity defined in the probe body, the cavity comprising an opening defined in an outer surface of the probe body, wherein the opening provides fluidic access to the cavity, and an agent channel defined within the cavity. The probe further comprises a contact disposed within the cavity, and an agent disposable within the agent channel.

Example 25 relates to the neural probe according to Example 24, wherein the agent channel is disposed around an outer circumference of the cavity.

Example 26 relates to the neural probe according to Example 24, wherein the agent is deliverable via contact with body fluids in fluidic communication with the cavity.

In Example 27, a positionable cortical electrode comprises a thin film pad, a plurality of electrode contacts disposed in the thin film pad, at least one delivery lumen defined in the thin film pad, a plurality of openings defined in an outer surface of the thin film pad, wherein the plurality of openings are in fluidic communication with the at least one delivery lumen, an elongate structure coupled to the thin film pad, and a fluid channel defined in the elongate structure, wherein the fluid channel is in fluidic communication with the at least one delivery lumen.

In Example 28, a neural probe comprises a probe body and a drug reservoir associated with the probe body, the drug reservoir comprising a reservoir body, a reservoir interior defined within the reservoir body, wherein the interior is configured to receive an agent, and an actuable gate disposed along an exterior wall of the reservoir body.

Example 29 relates to the neural probe according to Example 28, wherein the actuable gate comprises a conduit defined within the actuable gate, an opening defined in the actuable gate, wherein the opening is in fluid communication with the conduit, and a moveable flap disposed adjacent to the opening, wherein the moveable flap comprises an open position and a closed position in which the moveable flap is disposed over the opening.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

Discussed herein are various neural probes in the form of electrodes and other related devices, methods, and technologies that incorporate agent delivery of various kinds, including agent or drug elution. More specifically, the various embodiments disclosed or contemplated herein relate to improved systems, devices, and methods, and various components thereof, for monitoring, stimulating, and/or ablating brain tissue while also delivering an agent of some kind, and various components of such systems and devices. The agent can be delivered contemporaneously via drug delivery or over time (elution) via a coating or bioresorbable delivery of some kind, and can be a pharmaceutical drug or an agent for providing benefits to the patient, including, for example, enhancing the electrical features of the device. In some embodiments, the agent can be delivered or provided over time on the surface of the brain (via a cortical electrode, for example) or into the tissue of the brain (via a depth electrode, for example). In those implementations in which the agent is delivered or provided over time, it is understood that that it can be any known period of time, from a relatively short period to a relatively long period. In addition, the controlled delivery or providing of the agent according to any embodiment herein can be self-controlled by a patient, doctor, other user, or computer or can be controlled autonomously. For purposes of this application, it is understood that the term "drug delivery" includes elution.

Figure 1A:
FIG. 1A is a top view of a cortical electrode, according to one embodiment.
Figure 1B:
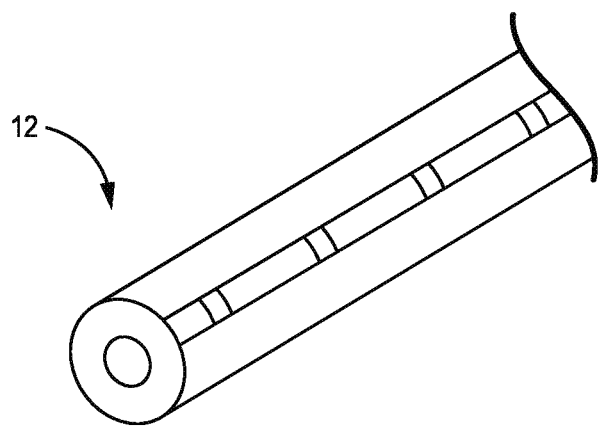
FIG. 1B is a perspective view of depth electrode, according to one embodiment.
Figure 1C:
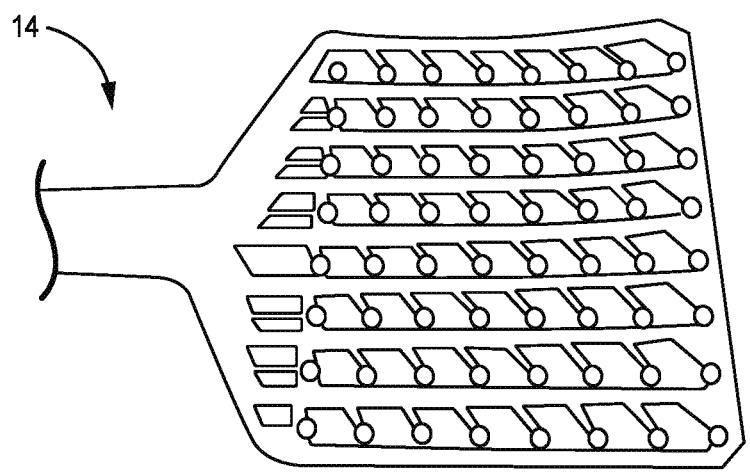
FIG. 1C is a perspective view of an electrode array, according to one embodiment.

The various drug delivery device embodiments disclosed or contemplated herein include any type of neural electrode, including, for example, a cortical electrode 10 as shown in FIG. 1A, a depth electrode 12 as depicted in FIG. 1B, or an electrode array 14 as shown in FIG. 1C. Other exemplary devices can include, for example, a scalp electrode (not shown). Alternatively, the implementations herein are not limited to those specific, exemplary devices. Rather, any of the drug delivery features or components disclosed or contemplated herein can be incorporated into any known neural probe or electrode. In each of these device embodiments as shown or any other known device, the drug delivery can be in the form of a coating disposed on at least a portion of the device (such as any of devices 10, 12, 14), with the coating containing a treatment agent or drug of some kind. Alternatively, as will be described in further detail below, the drug delivery can be accomplished via a sheath or other separate component that can be disposed over at least a portion of the device prior to implantation, deployed with the device, and released upon removal of the device to remain in position to continue to deliver a treatment agent over a predetermined period of time after the device has been removed. In a further alternative, the device itself can have an agent delivery component or feature, such as delivery openings in the device that allow for continual delivery over time or delivery upon actuation by a user. These agent delivery and elution embodiments and other such components or features are described in additional detail herein.

Figure 2:
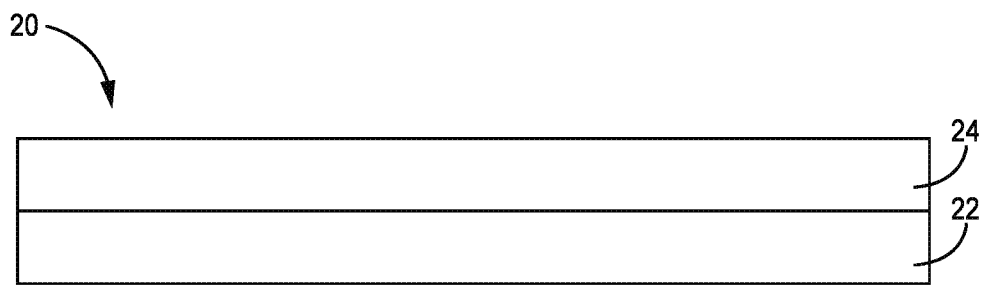
FIG. 2 is a side view of an outer surface of a neural probe device having an agent coating coated thereon, according to one embodiment.

In one embodiment as best shown in FIG. 2, the neural probe device 20 has an outer surface 22 with an agent coating 24 coated on the outer surface 22. It is understood that the neural probe device 20 can be any type of neural probe, including any of the exemplary devices discussed above, and it is further understood that the agent coating 24 embodiments as described herein can be incorporated into any device embodiment disclosed or contemplated herein. The outer surface 22 as shown can be any portion of the device 20, such that the entire outer surface 22 of the device 20 can be coated, or any portion thereof.

In one embodiment, the outer surface 22 of the device 20 is made of a polyimide, such as, for example, Kapton. In a further implementation, the outer surface 22 is made of parylene C, which is a coating that can be coated over the device 20 (including over a polyimide such as Kapton) to create the outer surface 22 made of parylene C. Alternatively, the outer surface 22 can be made of any known material that can be incorporated into a neural probe device 20.

In one specific embodiment, the coating 24 includes nitric oxide, and at least one treatment agent. That is, the treatment agent is coated onto the outer surface 22, and then the nitric oxide is coated over the treatment agent, thereby creating a two-layered agent coating 24 made up of the agent layer and the nitric oxide layer. After deployment of the device 20 to its desired location in the patient, the nitric oxide begins to slowly resolve over time, resulting in the slow release (elution) of the treatment agent. Alternatively, the coating 24 can include any composition that can slowly dissolve when the device 20 is deployed to slowly release the treatment agent over time. For example, the coating 24 can be a dissolvable coating, a hydrophilic coating, a patterned coating with time release, or any other type of coating. Alternatively, the coating 24 can including any composition that allows for release of the treatment agent via any period of time, including immediately.

In another exemplary implementation, the coating 24 is made up of a layer of time-release microspheres that contain the treatment agent and can release the treatment agent over a predetermined period of time that can be selected. That is, the microspheres can be engineered to release the agent over the desired time period, including, for example, a range from about one week to about one year. One specific example of such a microsphere that can be coated on the device 20 to create the coating 24 is the CHRONIJECT™ microsphere system for drug delivery, which is commercially available from Oakwood Labs.

In use, the device 20 would be positioned on or in the brain tissue of the patient, depending on the type of device 20. For example, a depth electrode device would be inserted into the brain tissue, while a cortical electrode would be positioned onto the surface of the brain tissue. Regardless of the type of device 20, the coating 24 with the treatment agent(s) contained therein is disposed on the outer surface 22 in a location on the device 20 so as to maximize the contact between the coating 24 and the brain tissue in contact with the device 20.

In one embodiment, the treatment agent included in the coating 24 is intended to curtail the body's response to the presence of the device in the body. For example, the treatment agent can be Slipskin™ 90/10 or Medikote™ PVD Coating. In certain implementations, the coating 24 provides for extended time-release of the treatment agent during the period of time that the device 20 is in the brain, thereby preventing or reducing the body's natural response to the presence of the device 20 throughout the time that the device 20 is present. The time-release feature of the coating 24 can be accomplished by the specific nitric oxide or microsphere technologies and similar technologies as discussed above, or by any other known time-release technology.

Alternatively, the treatment agent can be any known agent that could be beneficial for a neural probe in contact with brain tissue for any period of time. For example, the treatment agent can be heparin.

In addition to the desired benefits of the treatment agent included in the coating 24, additional benefits can arise from incorporation of the coating 24 onto the outer surface 22 of the device 20. For example, in certain embodiments, the coating 24 can increase contact between the brain tissue and the device 20 by causing the brain tissue to be attracted to the coating 24, thereby causing attraction of the brain tissue to the device 20. For example, in one embodiment, the coating 24 can be hydrophilic such that the coating attracts water, thereby causing the water in the brain tissue to be drawn toward and/or adhere to the device 20.

According to another implementation, the coating 24 can be used to influence or change the behavior of the electrical activity of a neuron. For example, in one embodiment, the coating 24 can influence the way ion channels in a neuron function. More specifically, the coating 24 can include a composition that contains ions, such as ions in the form of sodium or potassium, for example. Alternatively, the ion composition can be any known composition containing ions. A seizure is caused by neuron cells "firing" as a result of an increase in the action potential of the cells. The "firing" is a spark created by each cell as the cell is reset to bring the action potential back to a normal state. In this specific embodiment, the ion composition is delivered to the neuron cells such that the ions can change the ionic state outside the target neuron cells, thereby reducing or eliminating the risk of the cells firing. That is, the ions can bring the action potential of the cells back to a normal state without the cells firing. Thus, the coating 24 containing ions can decrease the electrical activity of one or more neurons, thereby reducing or eliminating the risk of a seizure. In certain embodiments, the coating 24 can contain a treatment agent that has both at least one drug in combination with ions.

Figure 10A:
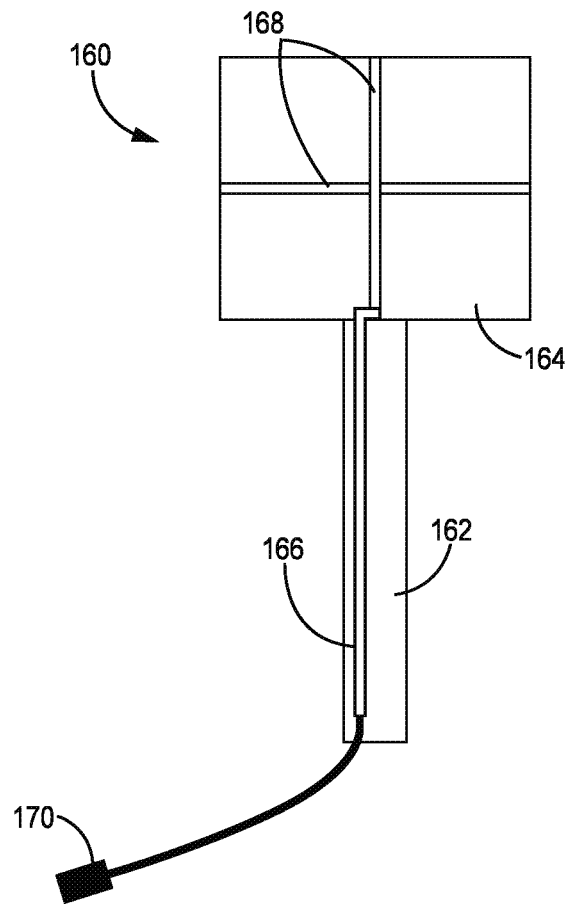
FIG. 10A is a top view of a cortical electrode with a fluidic agent delivery mechanism, according to one embodiment.
Figure 10B:
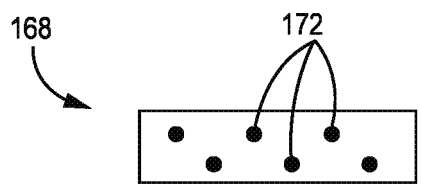
FIG. 10B is a side view of a portion of a delivery channel of a fluidic agent delivery mechanism, according to one embodiment.

In accordance with an alternative implementation as shown in FIGS. 10A and 10B, a device 160 is provided that can deliver a fluidic agent/composition via a delivery mechanism to slow seizure activity in a fashion similar to the delivery of ions as described above, but this embodiment utilizes cold saline or similar fluids instead of ions. As best shown in FIG. 10A, the device 160 in this implementation is a cortical electrode 160 having a connection structure 162 and an electrode array pad 164. Further, the device has a fluid channel 166 defined through the connection structure 162 and a delivery channel 168 defined in the electrode array pad 164 to provide for passage of the fluid agent through the channel 166 and delivery of the agent to the target area of the brain via the delivery channel 168. Further, the fluid channel 166 extends proximally from the connection structure 162 and has a connector 170 on its proximal end to allow for coupling to a syringe or other source of agent fluid.

In one implementation as shown, the delivery channel 168 has four branches extending across the pad 164 as shown. Alternatively, the delivery channel 168 can have one, two, three, or five or more branches. In a further alternative, the channel 168 can have any configuration that provides for effective delivery of the fluidic agent to the target area of the brain. As best shown in FIG. 10B, which depicts an expanded view of a portion of a delivery channel 168 according to one embodiment, the delivery channel 168 has a plurality of holes 172 formed therein such that the inner lumen (not shown) of the channel 168 is in fluidic communication with the area adjacent to the channel 168. As such, the fluidic agent being delivered through the fluid channel 166 and into the delivery channel 168 can pass through the holes 172 and thereby be delivered to the target area adjacent to the pad 164. It is understood that the holes 172 can be formed in the channel 168 along its entire length and all of its branches. Alternatively, the holes 172 can be formed in only a predetermine portion or length of the channel 168 and/or its branches.

According to certain embodiments, the fluidic agent is cold saline that can slow seizure activity by delivery to the area of the brain that is the source of that activity. Alternatively, any other fluidic agent that can slow seizure activity can be used.

In certain alternative implementations, the coating 24 can be added to or incorporate onto any type of neural tools (such that the outer surface 22 described above is an outer surface 22 of a related neural tool 20, rather than any of the probe or electrode embodiments discussed herein) that are used with or during use of neural probes, such as wands, spatulas, or other such known tools and devices. Thus, the various embodiments and features as described herein with respect to FIG. 2 can also apply to a coating 24 on any such tool, including any coating embodiment with any treatment agent as described or contemplated herein.

Figure 3A:
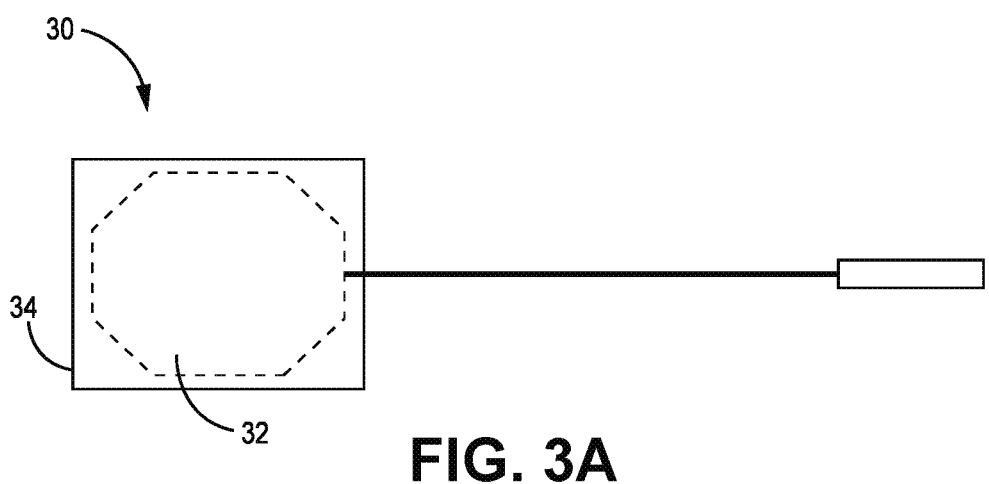
FIG. 3A is a top view of a cortical electrode with a drug delivery structure disposed thereon, according to one embodiment.
Figure 3B:
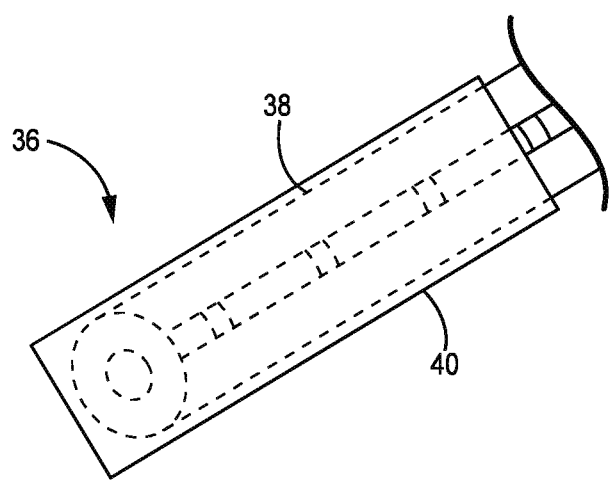
FIG. 3B is a perspective view of a depth electrode with a drug delivery structure disposed thereon, according to one embodiment.

FIGS. 3A and 3B depict two embodiments of neural probe devices 30, 36 having drug delivery components (or "structures") 34, 40 disposed thereon. More specifically, the device 30 in FIG. 3A is a cortical electrode 30 having a contact array 32, and the drug delivery structure 34 is disposed over the contact array 32. Further, the device 36 in FIG. 3B is a depth electrode 36 having an elongate body 38, and the drug delivery structure 40 is disposed over the elongate body 38. It is understood that a similar structure can be disposed over any neural probe device disclosed herein or any other known neural probe device. In these exemplary embodiments, in use, each structure 34, 40 can be a sheath, scaffold, or sheath-like structure 34, 40 that can be physically disposed over the device (such as device 30 or 36) prior to placement of the device on or in the patient's brain as necessary. Thus, when the device 30, 36 is positioned in the patient, the structure 34, 40 is also positioned in the patient. Further, in certain implementations, the structure 34, 40 can be maintained in place in the patient when the device 30, 36 is removed, thereby allowing the structure 34, 40 to continue to deliver the desired treatment agent to the area after the device 30, 36 is removed.

In certain embodiments, the structure 34, 40 (or any such structure for any type of neural probe device) can be a sheath or scaffold 34, 40 made of dissolvable material containing a treatment agent such that the treatment is steadily released over time as the material dissolves. For example, in one implementation, the structure 34, 40 is a commercially-available bioresorbable scaffold such as, or similar to, IGAKI-TAMAI™, DESOLVE®, DESOLVE® 100, IDEAL BIOSTENT™, REVA®, REZOLVE™, REZOLVE™ 2, FANTOM®, FORTITUDE®, MIRAGE™ BRMS, MERES™, XINSORB®, or ART 18AZ™ bioresorbable scaffolds. Alternatively, the structure 34, 40 can be any structure that can be made of any known dissolvable material for timed release of a treatment agent.

Figure 4:
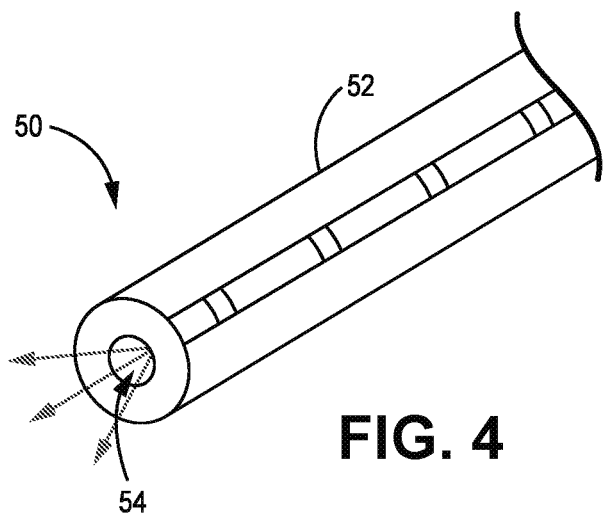
FIG. 4 is a perspective view of a depth electrode with a drug delivery lumen, according to one embodiment.

According to certain further implementations, any of the various device embodiments disclosed or contemplated herein can include a drug delivery component, structure, or feature that is integral to the device. For example, in one embodiment, a neural probe device 50 as depicted in FIG. 4 has a drug delivery lumen 54 defined in the body 52 of the device 50 such that the treatment agent can be delivered to the target area of the brain tissue via the drug delivery lumen 54 in the device 50 as shown. Further, as will be discussed in further detail below, in certain variations of this implementation, the device 50 can also have a delivery controller (similar to the controller/actuator 214 discussed in further detail below in relation to FIGS. 12A and 12B) associated with the device 50 that is in fluidic communication with the drug delivery lumen 54 such that the controller can actuate delivery of the treatment agent to the target area of the tissue via the lumen 54. Various exemplary controller implementations are discussed in further detail below.

It is understood that any device similar to device 50 having an agent delivery lumen such as lumen 54 can also be used for other types of fluid flow. That is, the fluidic access lumen 54 can be used to not only deliver a treatment agent, but also flush the treatment area with an appropriate known flushing fluid, or retract fluid from the treatment area via the lumen 54. In one specific exemplary embodiment, the fluidic access lumen 54 can be used to apply suction, thereby assisting with retaining the device 50 in place via the suction.

Figure 5:
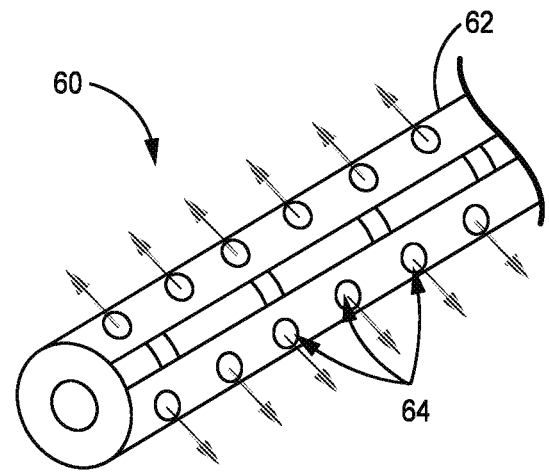
FIG. 5 is a perspective view of a depth electrode with small openings for delivery of an agent, according to one embodiment.

In further alternatives, instead of a delivery lumen (such as lumen 54 as discussed above), any device embodiment herein can have an array of small openings defined in the body of the device such that the treatment agent can be delivered to the treatment area via the small openings. One such exemplary device 60 is depicted in FIG. 5, in which the device 60 has openings 64 defined in the body 62 as shown. In use, any agent disclosed or contemplated herein can be delivered to the brain tissue via the openings 64. It is understood that the delivery can be accomplished via any delivery method or mechanism disclosed or contemplated herein. For example, any of the embodiments herein having small agent delivery openings can also have a controller/actuator similar to any of the exemplary embodiments discussed elsewhere herein such that delivery of the agent via the delivery openings can be controlled and actuated with precision.

According to the various embodiments herein, the treatment agent can be provided in any of several different forms for use with any of the device implementations disclosed or contemplated herein. For example, as described above, the agent can be provided in a liquid form that can vary in viscosity in the coating embodiments discussed above with respect to FIG. 2. Continuing with the coating embodiments of FIG. 2, it is understood that the agent can also be provided in a slurry form, a solid form, or any other form that a coating is known to take in the art. Alternatively, the agent can be provided in structured, water-soluble, non-fluid form in those embodiments in which the device has a drug delivery structure removably disposed thereon as discussed above with respect to FIGS. 3A and 3B. Alternatively, the agent can be provided in liquid form in those embodiments in which the device has a drug delivery structure, component, or feature integral to device as discussed above with respect to FIGS. 4 and 5. In a further embodiment, in the devices of FIGS. 4 and 5 (or any devices with any type of delivery structures), the treatment agent can be formed into a solid or dry form, such as a pellet or a powder. For example, in certain embodiments, the treatment agent is formed into a solid, water soluble pellet that can be delivered to the target area in the patient via the delivery lumen 54 of the device 50 in FIG. 4. In another example relating to the device 60 depicted in FIG. 5, the solid form of the treatment agent can be disposed within the device 60 such that fluid from the patient can come into contact with the solid treatment agent via the openings 64, thereby causing the solid treatment agent to begin to dissolve and thereby deliver the treatment agent to the target tissue via the openings 64. In accordance with another implementation similar to the water-soluble solid form as described above, the treatment agent can be in a liquid or dry form and disposed within a capsule. According to a further alternative, the agent can take any known form.

Other forms of drug delivery actuation are contemplated herein. For example, in certain implementations such as the exemplary implementation shown in FIG. 6, a system 70 is provided that includes a magnetic actuation member 74 that can operate in combination with the neural probe device 72 such that the magnetic actuation member 74 is in magnetic communication with the device 72. The magnetic communication allows the actuation member 74 to actuate the device 72 to release the treatment agent for delivery to the target area of the tissue. In this specific exemplary embodiment as shown, the probe 72 is a cortical electrode probe 72 having three layers 78A, 78B, 78C that are coupled together to form the body 78 of the probe 72. More specifically, the body 78 is made up of a first outer layer 78A, a middle or inner layer 78B, and a second outer layer 78C such that the middle layer 78B is disposed between and attached to the first and second outer layers 78A, 78C. The body 78 also has a cavity (also referred to herein as an "agent receptacle") 80 defined therein. More specifically, in this particular embodiment, the cavity 80 is formed via the absence of a length of the middle layer 70B, thereby resulting in a cavity 80 defined by the first layer 78A and the two opposing ends of the middle layer 70B on both sides of the cavity 80. Any treatment agent 82 according to any embodiment herein can be disposed in the cavity 80 as shown. The body 78 also has a deployable cover (or "flap") 84 that is disposed over the cavity 80 such that the cover 84 can be used to enclose the cavity 80 and thereby retain the agent 82 therein. Further, the flap 84 can be rotatably coupled to the body 78 by a joint 86 at one end of the flap 84. In a further alternative, the deployable cover 84 can be any known device or mechanism for covering an opening and being actuable to move into an open position.

In one embodiment, the flap 84 is tensioned such that the flap 84 is continuously urged toward the body 78 (in the direction indicated by arrow "A" toward the "closed" position in which the flap 84 is in contact with the body 78 and encloses the cavity 80) by the tension. Thus, as the flap 84 is urged away from the body 78 (in the direction indicated by arrow "B"), the force urging the flap 84 toward the body 78 increases. In one specific implementation, the tensioning component (not shown) is a spring or piston-like component (not shown). Alternatively, the tensioning component (not shown) can be any known tensioning component.

Figure 6:
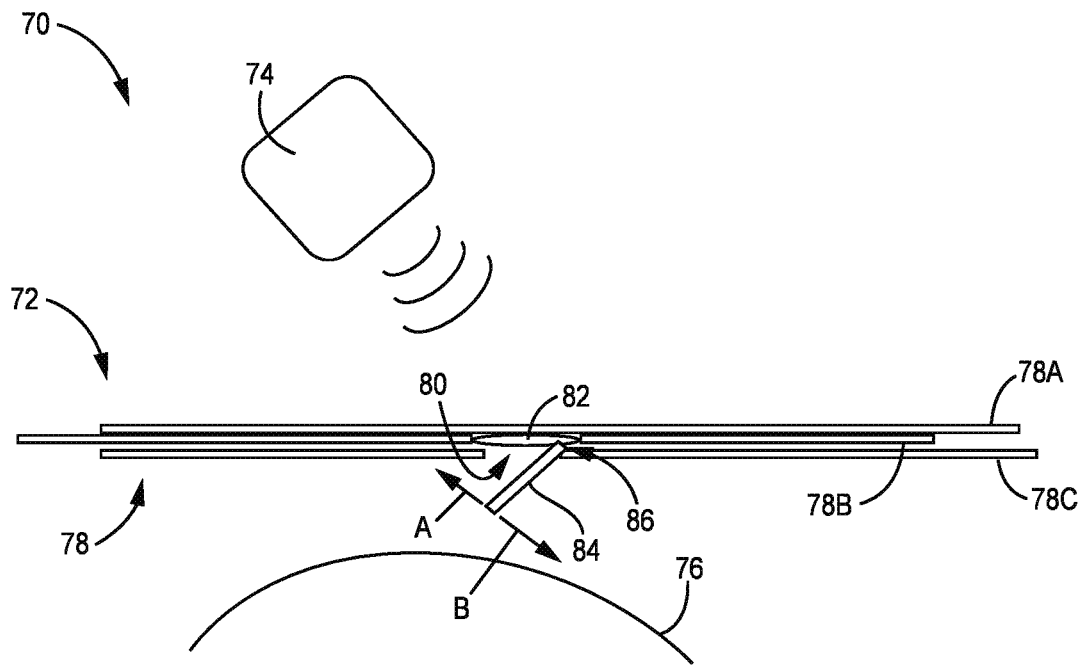
FIG. 6 is a cross-sectional side view of a drug delivery system that includes a neural probe device and a magnetic actuation member, according to one embodiment.

Further, the flap 84 in this implementation can be made of a magnetic material or can have a magnet or other magnetic material disposed therein (not shown) such that the magnetic actuation member 74 can communicate magnetically with the flap 84. Thus, in use, the device 72 can be positioned as needed in relation to the brain 76 of the patient. More specifically, in this example, the device 72 is disposed along the surface of the brain 76. Once the device 72 is positioned as desired, the treatment agent (or the composition containing the treatment agent) 82 in the cavity 80 can be released by application of a magnetic field via the magnetic actuation member 74. It is understood that the treatment agent 82 remains unreleased, or undelivered until the magnetic field is applied to the device 72. For example, as best shown in FIG. 6, the magnetic actuation member 74 is either moved by a user toward and into closer proximity with the device 72 or otherwise is actuated such that a magnetic field is generated by the actuation member 74 that extends to the flap 84. The flap 84 is repelled by the magnetic field, thereby causing the flap 84 to rotate on its hinge 86 away from the body 78 (in the direction indicated by arrow "B"). Thus, the rotation away from the body 78 causes the flap 84 to move into its open position or configuration, which results in fluidic access to the cavity 80. As a result, the magnetic actuation member 74 can be used to magnetically actuate the flap 84 to move into its open position, thereby releasing the agent 82 in the cavity 80.

Figure 7:
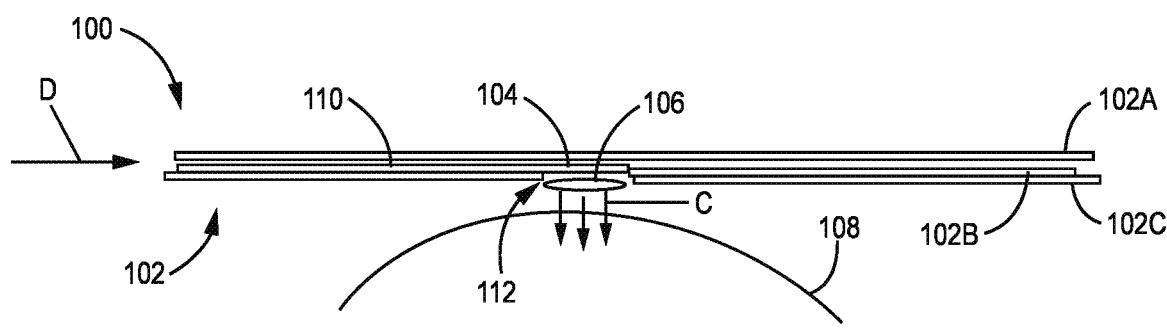
FIG. 7 is a cross-sectional side view of a iontophoretic drug delivery device, according to one embodiment.

In accordance with another drug delivery actuation embodiment, the treatment agent or the composition containing the treatment agent can be propelled or otherwise actuated to be delivered to the treatment area via iontophoresis. In one specific exemplary embodiment as depicted in FIG. 7, a device 100 is provided that has a device body 102 with a contact 104 that is also an electrical actuation member 104 that is in electrical communication with the treatment agent/composition 106 to be delivered to the target area of the brain 108. In this specific embodiment, the body 102 is made up of three layers: a first outer layer 102A, a middle or inner layer 102B, and a second outer layer 102C such that the middle layer 102B is disposed between and attached to the first and second outer layers 102A, 102C. A portion of the middle layer 102B is made up of the contact 104 and an electrical lead 110 coupled to the contact 104, as shown, such that an electrical current as represented by arrow D can be transmitted to the contact 104 via the lead 110. Alternatively, the contact and the electrical actuation member can be two different components. The body 102 also has a cavity (also referred to herein as an "agent receptacle") 112 defined therein. More specifically, in this particular embodiment, the cavity 112 is formed via the absence of a length of the second outer layer 102C, thereby resulting in a cavity 112 defined by the electrical actuation member/contact 104 and the two opposing ends of the second outer layer 102C on both sides of the cavity 112 such that the cavity 112 contains the contact 104, as discussed above. Any treatment agent 106 according to any embodiment herein that can be delivered via iontophoresis or any application of electrical current can be disposed in the cavity 112 as shown.

Thus, in the instant implementation as shown, the treatment agent/composition 106 is disposed in or on the device 100 such that actuation of the contacts (including contact 104) on the body 102 by providing an electrical current as represented by arrow D can interact with the ionically polarized treatment agent/composition 106 to propel the agent/composition 106 toward the treatment area of the brain 108, as represented by arrows C. Alternatively, it need not be the contacts of the electrode that propel the agent/composition. Instead, the device 100 can have any known component that can apply an electrical current to the agent/composition to propel the agent/composition in a similar fashion. In certain embodiments, regardless of the source of the actuation, the amount of current and/or time can be varied to control the speed and distance that the ionically polarized treatment agent/composition travels. Various iontophoretic delivery device embodiments can be scalp electrodes that are positioned on the external scalp of the patient, rather than inside the skull or in direct contact with the brain tissue. In these specific embodiments, the iontophoretic delivery makes it possible to deliver the treatment agent through the skull.

Figure 8:
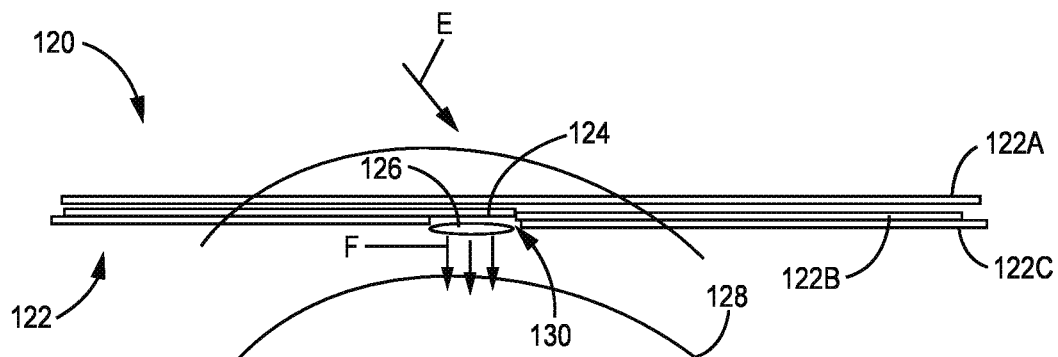
FIG. 8 is a cross-sectional side view of a kinetic energy drug delivery device, according to one embodiment.

In a further alternative embodiment of a drug delivery actuation embodiment as shown in FIG. 8, the treatment agent or the composition containing the treatment agent can be propelled or otherwise actuated to be delivered to the treatment area via kinetic energy. More specifically, a device 120 is provided that has a device body 122 with a contact 124 that is also an kinetic actuation member 124 that is in contact with or otherwise in communication with the treatment agent/composition 126 to be delivered to the target area of the brain 128. In this specific embodiment, the body 122 is made up of three layers: a first outer layer 122A, a middle or inner layer 122B, and a second outer layer 122C such that the middle layer 122B is disposed between and attached to the first and second outer layers 122A, 122C. A portion of the middle layer 122B is made up of the contact 124 that can be made of a material that is responsive to kinetic energy such that kinetic energy as represented by arrow E can be transmitted to the contact 124 and cause the contact/kinetic actuation member 124 to urge the agent/composition 126 toward the brain 128. Alternatively, the contact and the kinetic actuation member can be two different components. The body 122 also has a cavity (also referred to herein as an "agent receptacle") 130 defined therein. More specifically, in this particular embodiment, the cavity 130 is formed via the absence of a length of the second outer layer 122C, thereby resulting in a cavity 130 defined by the kinetic actuation member/contact 124 and the two opposing ends of the second outer layer 122C on both sides of the cavity 130 such that the cavity 130 contains the contact 124, as discussed above. Any treatment agent 126 according to any embodiment herein that can be delivered via kinetic energy or any application of kinetic energy—such as vibration, tuned vibration, ultrasound, etc.—can be disposed in the cavity 130 as shown.

Thus, in the instant implementation as shown, the treatment agent/composition 126 is disposed in or on the device 120 such that actuation of the contacts (including contact 124) on the body 122 by providing kinetic energy as represented by arrow E can interact with the treatment agent/composition 126 to propel the agent/composition 126 toward the treatment area of the brain 128, as represented by arrows F. Alternatively, it need not be the contacts of the electrode that propel the agent/composition. Instead, the device 120 can have any known component that can apply kinetic energy to the agent/composition to propel the agent/composition in a similar fashion. In certain embodiments, regardless of the source of the actuation, the amount of energy and/or time can be varied to control the speed and distance that the treatment agent/composition travels.

Figure 9A:
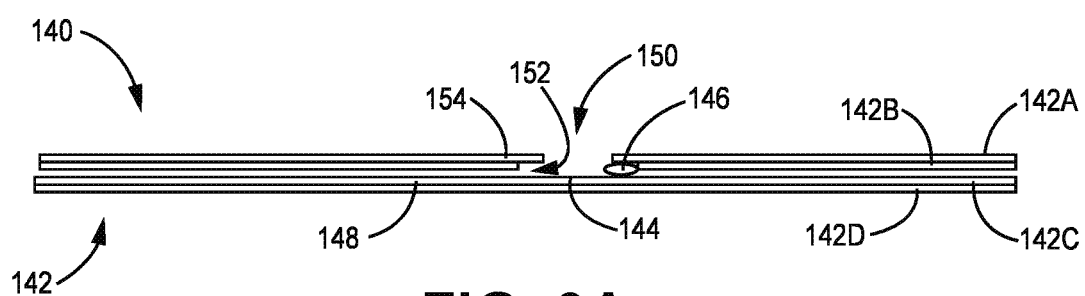
FIG. 9A is a cross-sectional side view of a drug delivery device with a cavity having an agent channel, according to one embodiment.
Figure 9B:
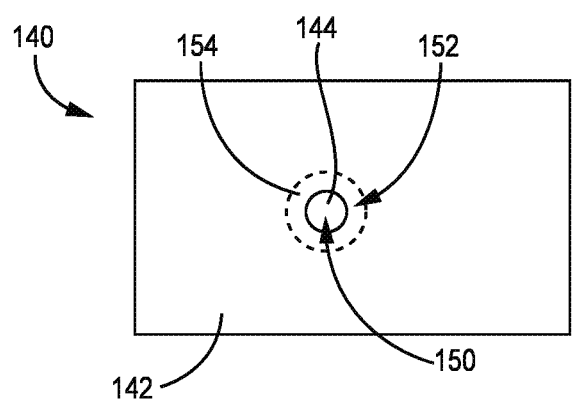
FIG. 9B is a top view of the drug delivery device of FIG. 9A, according to one embodiment.

Another embodiment of a drug delivery device is contemplated that doesn't require external actuation, but simply provides for delivery of the agent via fluidic access to the agent such that the agent is dissolved over time into the brain fluids that contact the agent. More specifically, as shown in FIG. 9A (cross-sectional side view) and 9B (top view), a device 140 is provided that has a device body 142 with a contact 144 disposed within a cavity 150 that defines an agent channel 152 within the cavity 150 such that an agent/composition 146 can be disposed within the channel 152. Please note that the agent/composition 146 is only depicted in a portion of the channel 152 in FIG. 9A in order to be able to better depict the channel 152 in the portion not containing any agent 146. In this specific embodiment, the body 142 is made up of four layers: a first outer layer 142A, a middle or inner layer 142B, a lead and contact layer 142C, and a second outer layer 142D such that the middle layer 142B and the lead/contact layer 142C are disposed between and attached to the first and second outer layers 142A, 142D. The lead/contact layer 142C is made up of the contact 144 and a lead component 148 that is coupled to the contact 144 and delivers electrical stimulation thereto. The cavity 150 is formed via the absence of a length of the first outer layer 142A and a length of the middle layer 142B, thereby resulting in a cavity 150 defined by the contact 144 and the two opposing ends of the first outer layer 142A and of the middle layer 142B on both sides of the cavity 150 such that the cavity 150 contains the contact 144, as discussed above. Further, the agent channel 152 defined within the cavity 150 such that the channel 152 encircles the cavity 150 is formed by the lip 154 that is formed via the first outer layer 142A. More specifically, the first outer layer 142A extends further towards the center of the cavity 150 in comparison to the middle layer 142B such that the lip 154 is formed around the circumference of the cavity 150. As such, the lip 154 forms the channel 152 such that the agent 146 can be disposed within the channel 152 and thereby be disposed around the outer circumference of the cavity 150 (and the contact 144). Any treatment agent 146 according to any embodiment herein that can be delivered via fluidic access can be disposed in the cavity 150 as shown.

Thus, in the instant implementation as shown, the treatment agent/composition 146 is disposed with the channel 154 in the device 140 as described above such that liquid in the brain tissue can enter the cavity 150 and interact with the treatment agent/composition 146, causing the agent/composition 146 to dissolve over some predetermined period of time and thereby be delivered to the target area of the brain adjacent to the cavity 150. Alternatively, this device 140 can incorporate iontophoretic or kinetic energy delivery technology similar to that described above into the device 140 such that the agent/composition 146 in the channel 154 can be delivered by iontophoretic or kinetic energy actuation.

Figure 11A:
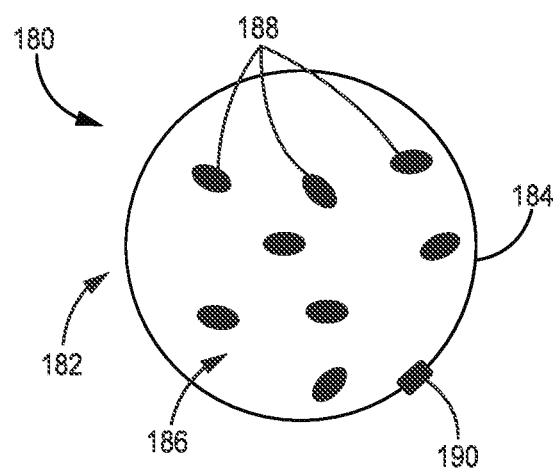
FIG. 11A is a cross-sectional side view of a drug delivery reservoir, according to one embodiment.
Figure 11B:
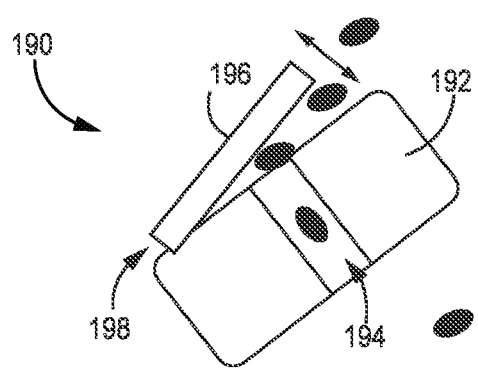
FIG. 11B is a side view of the actuable gate of the reservoir of FIG. 11A, according to one embodiment.

Another form of drug delivery, according to a further implementation, relates to timed release of an agent via an agent reservoir, as depicted with respect to one example in FIGS. 11A and 11B. In this exemplary implementation, a drug reservoir 180 is provided that can be integrated into a contact of any neural probe or alternatively can be disposed elsewhere on the probe. The reservoir 180 has an enclosure (or "body") 182 with a wall 184 that defines an interior 186 that contains the desired agent 188. Further, an actuable gate 190 is provided at some point along the wall 184 such that the gate 190 can be actuated to allow for release of some portion (or all) of the agent from the reservoir 180 at the desired time. As best shown in FIG. 11B, according to one embodiment, the gate 190 has a body 192, a conduit 194 defined through the body 192, and a moveable flap 196. The movable flap 196 has a hinge 198 such that it is rotatably coupled to the body 192 and can move between a closed position (or "configuration) in which it is disposed over the conduit 194 and thereby seals the conduit 194 closed and an open position (or "configuration") in which it is positioned away from the body 192 as depicted, thereby allowing fluidic access to the conduit 194 and thus allowing passage of agent out of the interior 186, through the conduit 194, and out to the target tissue.

In one embodiment, the flap 196 is operated magnetically and is tensioned to return to its closed position when any external forces are removed, in a fashion similar to the flap 84 described above. Alternatively, the flap 196 can be operated mechanically, electrically, or via any form of force. Further, while the specific gate 190 has been described in detail, it is understood that any type of known port or door that can provide both open and closed configurations can be incorporated into the reservoir for use herein. In addition, it is understood that an external actuation mechanism is in communication with the gate 190 such that a user can utilize the external actuation mechanism to control the gate 190 via any form of communication, including wired or wireless communication.

Figure 12A:
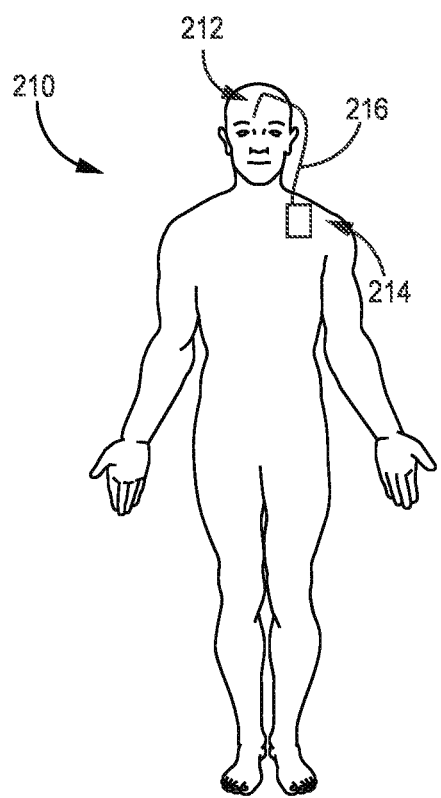
FIG. 12A is a schematic view of a drug delivery system having a neural probe coupled to a controller, according to one embodiment.
Figure 12B:
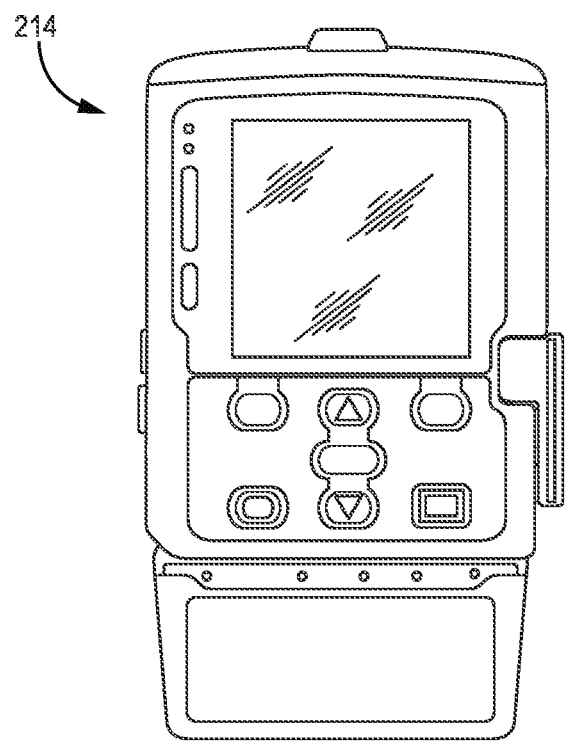
FIG. 12B is a front view of a known controller for use with the system of FIG. 12A, according to one embodiment.

Another drug delivery system 210 is depicted in FIGS. 12A and 12B, according to one exemplary implementation. The system 210 has a neural probe 212 that is coupled to a controller 214 via a connection line 216. In one exemplary embodiment, the controller 214 is a known drug pump 214 as best shown in FIG. 12B. The drug pump 214 can be any known drug/infusion pump 214 that can be used to deliver any agent to a patient over time and further can provide precise control of said delivery. Alternatively, any known controller/actuation device can be incorporated into the system 210. The controller 214 is coupled with the neural probe 212 via the connection line 216 such that the controller 214 can control the operation of the probe 212, including controlling the delivery of an agent from the probe 212 to the brain of the patient. In one embodiment, the connection line 216 has at least one communication line (not shown) and at least one agent delivery lumen (not shown) disposed therein, such that the connection line 216 can be used to transmit electronic or electrical communications via the communication line and further can be used to transfer an agent via the agent delivery lumen. In one embodiment, the neural probe 212 is a depth electrode 212. Alternatively, the neural probe 212 can be any known probe, including a cortical electrode or any other known probe.

It is understood that any of the device embodiments with a drug delivery lumen as disclosed or contemplated herein, including those in FIGS. 4, 5, 10A, 10B, 11A, and 11B, can be coupled with and operate in conjunction with a controller/actuator such as the controller/actuator 214 described above. Further, any other embodiment having an actuable component can also be coupled with an operate in conjunction with a controller/actuator, including those in FIGS. 6-9B. As such, any of the device implementations disclosed or contemplated herein can be incorporated into the system 210 or any similar system having a controller/actuator.

It is further understood that any of the various embodiments disclosed or contemplated in FIGS. 2-12B can be incorporated into or used in conjunction with any known neural probe embodiment, including the embodiments depicted in FIGS. 1A-1C.

In use, the various devices disclosed or contemplated herein, including those having a delivery lumen, delivery openings, iontophoretic delivery, kinetic energy delivery, fluidic access delivery, agent reservoirs, or similar structures or features, can be used to treat a seizure in real-time. That is, if a patient feels a seizure coming on, the patient can actuate a controller/actuator (similar to any of the controller/actuator embodiments discussed above, for example), or the controller can otherwise be triggered to actuate the implanted probe to deliver a treatment agent into the brain tissue via the agent delivery component (such as an agent delivery lumen or agent delivery openings as described above, for example) to eliminate or minimize the seizure. Alternatively, the various delivery components can be utilized in any known manner to deliver a treatment agent via a neural probe device as disclosed or contemplated herein.

Various treatment agents can be incorporated into any of the various drug delivery device embodiments disclosed or contemplated herein. For example, some of the exemplary treatment agents can include, but are not limited to, paclitaxel (available as ELUTAX™, BIOSTREAM™, PANTERALUX™, etc.), acetazolamide, brivaracetam (available as BRIVIACT™), carbamazepine (also available as CARBAGEN™ TEGRETOL™, TEGRETOL PROLONGED RELEASE™), clobazam (also available as FRISIUM™, PERIZAM™, TAPCLOB™, ZACCO™), clonazepam, eslicarbazepine acetate (available as ZEBINIX™) ethosuximide, gabapentin (also available as NEURONTIN™), lacosamide (available as VIMPAT™), lamotrigine (also available as LAMITCAL™), levetiracetam (also available as DESITREND™, KEPPRA™) oxcarbazepine (also available as TRILEPTAL™), perampanel (available as FYCOMPA™), phenobarbital, phenytoin (also available as EPANUTIN™, PHENYTOIN SODIUM FLYNN™) piracetam (available as NOOTROPIL™), pregabalin (also available as ALZAIN™, AXALID™, LECAENT™, LYRICA™, REWISCA™), primidone, rufinamide (available as INOVELON™), sodium valproate (also available as EPILIM™, EPILIM CHRONO™, EPILIM CHRONOSPHERE™, EPISENTA™, EPIVAL™), stiripentol (also available as DIACOMIT™), tiagabine (available as GABITRIL™), topiramate (also available as TOPAMAX™), valproic acid (available as CONVULEX™, EPILIM CHRONO™, EPILIM CHRONOSPHERE™), vigabatrin (available as SABRIL™), zonisamide (also available as ZONE-GRAN™), any cannabinoid, any antibiotic, and any stem cell composition. It is further understood that the agent can be any known seizure treatment agent or any other treatment agent that could benefit a patient into which an electrode device is being implanted.

In certain embodiment, the treatment agent can be a seizure treatment agent that is attracted to electrical activity. For example, the agent can have an ionic attraction to the misfiring cells in the brain tissue, thereby resulting in the agent being drawn to the area that is the source of the seizure. In one example, the agent is an electrically charged molecule polarized agent (similar to the types of agents used in iontophoretic delivery). Alternatively, the agent takes the form of an electrically charged sphere coated with the agent. In a further alternative, the agent can be any known seizure treatment agent that is attracted to electrical activity, including any agents that have been polarized to be drawn to electrical potentials in a tissue. In these embodiments, the agent can be released or delivery by any of the device embodiments disclosed or contemplated herein and then will be attracted to an area of electrical activity, which is likely to be a seizure. Further, it is understood that, according to various implementations, the agent is an agent that helps to normalize the neuron action potential of the misfiring cells. As such, the agent is drawn to the seizure, where it treats the seizure.

In further implementations, the agent is not a treatment agent, but instead is an indication agent or other type of agent that can be incorporated into or delivered via any embodiment disclosed or contemplated herein. In one specific example, the agent is a blood indication agent. That is, the agent is a composition that changes color in the presence of protein, thereby indicating the presence of blood. In one example, the blood indication agent can change color to notify a surgeon that there is blood present in the surgical area of the patient.

Although the present invention has been described with reference to preferred embodiments, persons skilled in the art will recognize that changes may be made in form and detail without departing from the spirit and scope of the invention.

What is claimed is:

1. A neural electrode comprising:
   (a) an electrode body;
   (b) at least one electrode array associated with the electrode body; and
   (c) a dissolvable agent delivery structure releasably disposed over at least a portion of the electrode body such that the dissolvable agent delivery structure is configured to separate from the electrode body and remain in a treatment position upon removal of the electrode body.

2. The neural electrode of claim 1, wherein the dissolvable agent delivery structure is configured to deliver a treatment agent over a predetermined period of time following removal of the electrode body.

3. The neural electrode of claim 1, wherein the dissolvable agent delivery structure comprises a dissolvable scaffold comprising at least one treatment agent.

4. The neural electrode of claim 3, wherein the at least one treatment agent is releasable over time as the dissolvable scaffold dissolves.

5. The neural electrode of claim 3, wherein the at least one treatment agent comprises a cannabinoid.

6. The neural electrode of claim 1, wherein the electrode body comprises an elongate, unitary tubular body, wherein the at least one electrode array is disposed on an outer surface of the tubular body, and wherein the neural electrode is a depth electrode.

7. The neural electrode of claim 1, further comprising an elongate structure coupled to the electrode body, wherein the electrode body comprises a thin film pad, wherein the at least one electrode array is disposed in the thin film pad, and wherein the neural electrode is a cortical electrode.

8. A neural electrode comprising:
   (a) an electrode body;
   (b) at least one electrode associated with the electrode body; and
   (c) a dissolvable agent delivery structure releasably disposed over at least a portion of the electrode body such that the dissolvable agent delivery structure is configured to be deployed with the electrode body and then released from the electrode body, and to remain in a treatment position upon removal of the electrode body.

9. The neural electrode of claim 8, wherein the dissolvable agent delivery structure is configured to deliver a treatment agent over a predetermined period of time following removal of the electrode body.

10. The neural electrode of claim 8, wherein the dissolvable agent delivery structure comprises a dissolvable scaffold comprising at least one treatment agent.

11. The neural electrode of claim 10, wherein the at least one treatment agent is releasable over time as the dissolvable scaffold dissolves.

12. The neural electrode of claim 10, wherein the at least one treatment agent comprises a cannabinoid.

13. The neural electrode of claim 8, wherein the electrode body comprises an elongate, unitary tubular body, and wherein the at least one electrode is disposed on an outer surface of the tubular body, and wherein the neural electrode is a depth electrode.

14. The neural electrode of claim 8, further comprising an elongate structure coupled to the electrode body, wherein the electrode body comprises a thin film pad, wherein the at least one electrode is disposed in the thin film pad, and wherein the neural electrode is a cortical electrode.

15. The neural electrode of claim 14 wherein the elongate structure comprises a proximal end, a distal end, and a fluid channel extending from the proximal end to the distal end, wherein the distal end of the elongate structure is coupled to the electrode body.

16. The neural electrode of claim 15 wherein the fluid channel is in fluid communication with a drug delivery lumen defined in a portion of the electrode body.

17. The neural electrode of claim 14 further comprising an agent elution coating disposed on the electrode body.

18. A method of using a neural electrode, the method comprising:
   (a) providing the neural electrode, the neural electrode comprising:
      (i) an electrode body;
      (ii) at least one electrode array associated with the electrode body; and
      (iii) a dissolvable agent delivery structure releasably disposed over at least a portion of the electrode body such that the dissolvable agent delivery structure is configured to release from the electrode body and remain in a treatment position upon removal of the electrode body;
   (b) deploying the electrode body and the dissolvable agent delivery structure to the treatment position;
   (c) releasing the dissolvable agent delivery structure from the electrode body; and (d) removing the electrode body from the treatment position.

* * * * *